(12) United States Patent
Brockway et al.

(10) Patent No.: US 7,433,853 B2
(45) Date of Patent: Oct. 7, 2008

(54) EXPERT SYSTEM FOR PATIENT MEDICAL INFORMATION ANALYSIS

(75) Inventors: Marina Brockway, Shoreview, MN (US); Gerrard M. Carlson, Champlin, MN (US); Veerichetty Kadhiresan, Centerville, MN (US); Vladimir Kovtun, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 366 days.

(21) Appl. No.: 10/889,353

(22) Filed: Jul. 12, 2004

(65) Prior Publication Data

US 2006/0010090 A1    Jan. 12, 2006

(51) Int. Cl.
*G06N 5/04* (2006.01)

(52) U.S. Cl. ............... 706/45; 706/46; 706/47; 706/52; 600/300; 600/301

(58) Field of Classification Search ............ 706/1, 706/8, 10–15, 21, 22, 45; 600/16–18, 300, 600/301, 481–485, 508–515, 529; 607/6, 607/9, 14, 17–19, 27, 28, 32
See application file for complete search history.

(56) References Cited

U.S. PATENT DOCUMENTS

| | | | |
|---|---|---|---|
| 5,251,626 A | 10/1993 | Nickolls et al. | |
| 5,262,944 A | 11/1993 | Weisner et al. | |
| 5,518,001 A | * | 5/1996 | Snell .................. 600/510 |
| 5,542,430 A | 8/1996 | Farrugia et al. | |
| 5,549,654 A | 8/1996 | Powell | |
| 5,819,007 A | 10/1998 | Elghazzawi | |
| 5,911,132 A | 6/1999 | Sloane | |
| 6,024,705 A | 2/2000 | Schlager et al. | |
| 6,042,548 A | 3/2000 | Giuffre | |
| 6,221,011 B1 | 4/2001 | Bardy | |
| 6,272,377 B1 | 8/2001 | Sweeney et al. | |
| 6,312,378 B1 | 11/2001 | Bardy | |
| 6,363,282 B1 | 3/2002 | Nichols et al. | |
| 6,400,982 B2 | 6/2002 | Sweeney et al. | |
| 6,442,432 B2 | 8/2002 | Lee | |
| 6,443,890 B1 | 9/2002 | Schulze et al. | |
| 6,480,745 B2 | 11/2002 | Nelson et al. | |
| 6,497,655 B1 | 12/2002 | Linberg et al. | |

(Continued)

FOREIGN PATENT DOCUMENTS

WO    WO-01/24876 A1    4/2001

(Continued)

OTHER PUBLICATIONS

Charniak, E., et al., "Bayesian Networks Without Tears", *Al Magazine*, (1991),50-63.

(Continued)

*Primary Examiner*—David Vincent
*Assistant Examiner*—Omar F Fernanadez
(74) *Attorney, Agent, or Firm*—Schwegman, Lundberg & Woessner, P.A.

(57) ABSTRACT

A plurality of chronic sensors are used to facilitate diagnosis and medical decision making for an individual patient. An expert system evaluates the sensor data, combines the sensor data with stored probability data and provides an output signal for notification or medical intervention.

33 Claims, 6 Drawing Sheets

U.S. PATENT DOCUMENTS

| | | | |
|---|---|---|---|
| 6,533,724 B2 | 3/2003 | McNair | |
| 6,564,104 B2 | 5/2003 | Nelson et al. | |
| 6,574,511 B2 | 6/2003 | Lee | |
| 6,577,901 B2 | 6/2003 | Thompson | |
| 6,602,191 B2 | 8/2003 | Quy | |
| 6,622,045 B2 | 9/2003 | Snell et al. | |
| 6,648,823 B2 | 11/2003 | Thompson et al. | |
| 6,650,939 B2 | 11/2003 | Taepke, II et al. | |
| 6,650,944 B2 | 11/2003 | Goedeke et al. | |
| 6,656,125 B2 * | 12/2003 | Misczynski et al. | 600/508 |
| 6,669,631 B2 | 12/2003 | Norris et al. | |
| 6,671,547 B2 | 12/2003 | Lyster et al. | |
| 7,050,846 B2 | 5/2006 | Sweeney et al. | |
| 7,127,290 B2 | 10/2006 | Girouard et al. | |
| 7,184,817 B2 | 2/2007 | Zhu et al. | |
| 7,184,837 B2 | 2/2007 | Goetz | |
| 7,200,435 B2 | 4/2007 | Ricci et al. | |
| 7,289,761 B2 | 10/2007 | Mazar et al. | |
| 2001/0039375 A1 | 11/2001 | Lee et al. | |
| 2002/0019586 A1 | 2/2002 | Teller et al. | |
| 2002/0032386 A1 * | 3/2002 | Sackner et al. | 600/536 |
| 2002/0082868 A1 | 6/2002 | Pories et al. | |
| 2002/0099302 A1 | 7/2002 | Bardy et al. | |
| 2002/0115939 A1 | 8/2002 | Mulligan et al. | |
| 2002/0120311 A1 | 8/2002 | Lindh et al. | |
| 2002/0123673 A1 * | 9/2002 | Webb et al. | 600/300 |
| 2002/0138012 A1 | 9/2002 | Hodges et al. | |
| 2003/0074029 A1 | 4/2003 | Deno et al. | |
| 2003/0083717 A1 | 5/2003 | Mlynski et al. | |
| 2003/0088290 A1 | 5/2003 | Spinelli et al. | |
| 2004/0100376 A1 * | 5/2004 | Lye et al. | 340/539.12 |
| 2004/0103001 A1 | 5/2004 | Mazar et al. | |
| 2004/0122294 A1 | 6/2004 | Hatlestad et al. | |
| 2004/0122295 A1 | 6/2004 | Hatlestad et al. | |
| 2004/0122296 A1 | 6/2004 | Hatlestad et al. | |
| 2004/0122297 A1 | 6/2004 | Stahmann et al. | |
| 2004/0122484 A1 | 6/2004 | Hatlestad et al. | |
| 2004/0122485 A1 | 6/2004 | Stahmann et al. | |
| 2004/0122486 A1 | 6/2004 | Stahmann et al. | |
| 2004/0128161 A1 * | 7/2004 | Mazar et al. | 705/2 |
| 2005/0065569 A1 * | 3/2005 | Ricci et al. | 607/32 |
| 2005/0101841 A9 * | 5/2005 | Kaylor et al. | 600/300 |
| 2006/0200007 A1 | 9/2006 | Brockway et al. | |
| 2006/0271116 A1 | 11/2006 | Stahmann et al. | |
| 2007/0067005 A1 | 3/2007 | Schatz et al. | |
| 2007/0106129 A1 | 5/2007 | Srivathsa et al. | |
| 2007/0156187 A1 | 7/2007 | Ricci et al. | |
| 2007/0260285 A1 | 11/2007 | Libbus et al. | |
| 2008/0024294 A1 | 1/2008 | Mazar et al. | |

FOREIGN PATENT DOCUMENTS

| | | |
|---|---|---|
| WO | WO-2006/127719 A2 | 11/2006 |
| WO | WO-2006/127719 A3 | 11/2006 |
| WO | WO-2007/133873 A2 | 11/2007 |
| WO | WO-2007/133873 A3 | 11/2007 |

OTHER PUBLICATIONS

Diez, F. J., et al., "Diaval, a Bayesian Expert System for Echocardiography", 1-13, Date not Known.

Niedermayer, D., et al., "An Introduction to Bayesian Networks and their Contemporary Applications", (Observed on Jan. 13, 2004), 14 pages.

* cited by examiner

EXPERT SYSTEM FOR PATIENT MEDICAL INFORMATION ANALYSIS

TECHNICAL FIELD

This document pertains generally to remote patient monitoring using implantable medical devices, and more particularly, but not by way of limitation, to an expert system for analysis or management of chronic medical conditions.

BACKGROUND

Heart failure patients are often on a regimen including various drugs that control the symptoms of heart failure and maintain neuro-hormonal balance. For some drugs, the level is optimized (for example, diuretics) or up-titrated to the target dosage. Imbalance between the various drugs, their side effects, patient diet and other factors can lead to decompensation and costly hospitalization. Cardiac decompensation is typically marked by dyspnea (difficulty breathing), venous engorgement and edema and each decompensation event causes further long term deterioration of the heart function. Furthermore, maintenance of the proper regimen requires frequent contact with the patient that consumes signification medical resources.

BRIEF DESCRIPTION OF THE DRAWINGS

In the drawings, which are not necessarily drawn to scale, like numerals describe substantially similar components throughout the several views. Like numerals having different letter suffixes correspond to different instances of substantially similar components. The drawings illustrate generally, by way of example, but not by way of limitation, various embodiments of the present subject matter.

DETAILED DESCRIPTION

Figure 1:
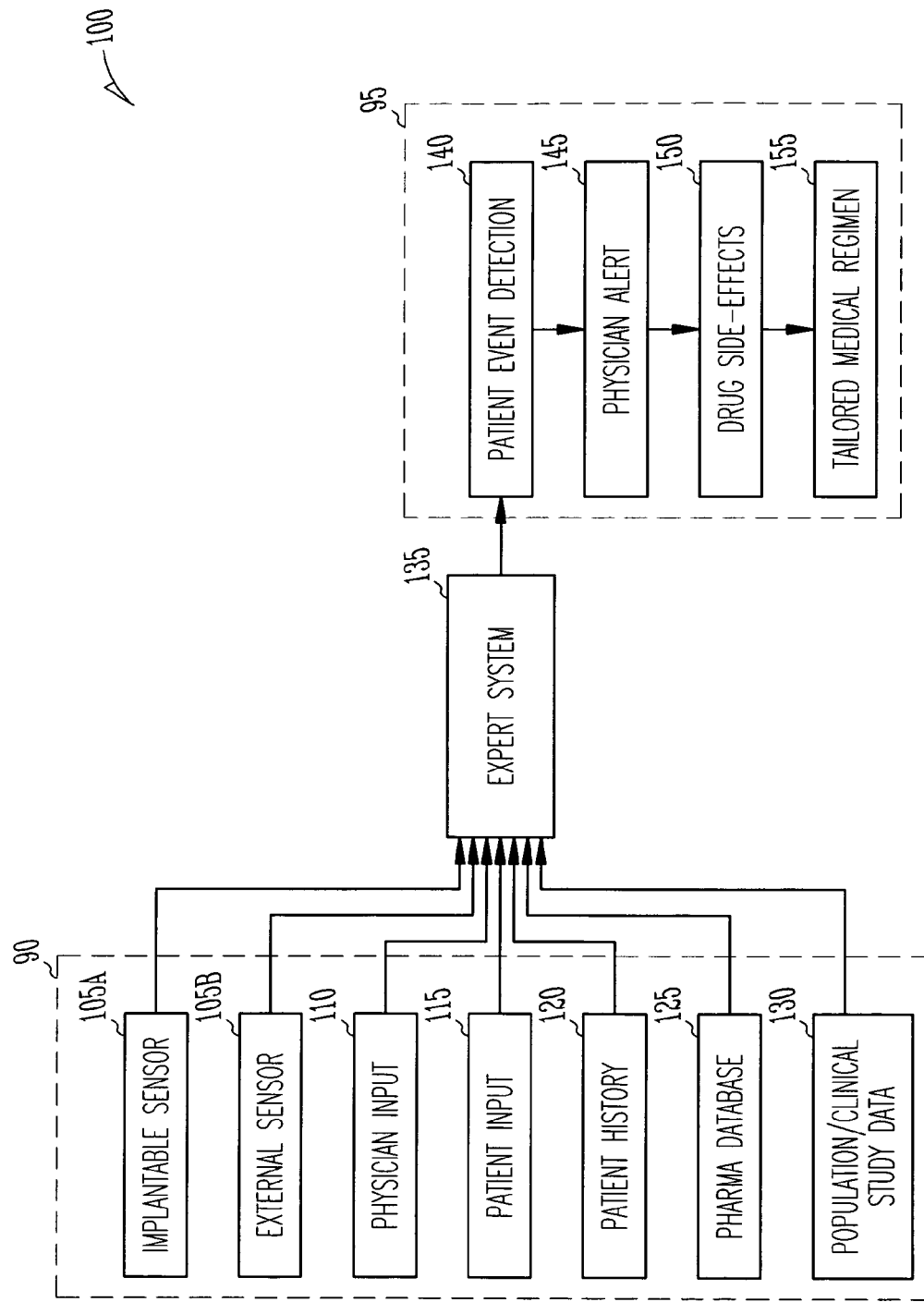
FIG. 1 illustrates a block diagram of an exemplary system.

In the following detailed description, reference is made to the accompanying drawings which form a part hereof and which illustrate specific embodiments of the present subject matter. The various examples are described in sufficient detail to enable those skilled in the art to practice the subject matter, and it is to be understood that the examples may be combined, or that other examples may be utilized and that structural, logical and electrical changes may be made without departing from the scope of the present subject matter. The detailed description is, therefore, not to be taken in a limiting sense and the scope of the present subject matter is defined by the appended claims and their equivalents.

In this document, the articles "a" and "an" denote both the singular and the plural form of the associated noun, and, unless otherwise noted, the term "or" is used in the non-exclusive sense. Furthermore, all publications, patents, and documents referred to in this document are incorporated by reference herein in their entirety, as though individually incorporated by reference. In the event of inconsistencies between this document and those publications, patents and documents herein incorporated by reference, this document is controlling.

System Introduction

The present systems and methods provide remote monitoring of patients in an ambulatory setting using data from a combination of implantable and external sensors. In one example, a variety of sensor signals are continuously monitored and the data is collected in real time. The data, in one example, is processed by an expert system and upon certain conditions, an alert notification is sent to a physician or a patient. The sensor data is conveyed via the internet or other communication network. In one example, an implantable device is coupled to a remote interrogation device (sometimes referred to as a repeater) located in the patient's home or other facility and the data is sent by a computer (internet, network, phone line) to the expert system.

A combination of sensors provide chronic patient data under various conditions and measured in various manners. For example, a combination of sensor data is used to detect the patient's hemodynamic state and facilitate assessment of congestion, perfusion, contractility or various other conditions. In one example, heart failure or other conditions are assessed.

In one example, the system includes an inference engine which assembles the information coming from different sources and provides a concise summary to enable a physician or other medical personnel to monitor the patient. The different sources, in various examples, includes implantable sensors as well as external sensors. For example, the expert system is configured to detect the presence of a drug side effect.

In one example, the system is configured for monitoring chronic diseases other than heart failure, including, for instance, diabetes or cancer. In one example, more than one expert system is provided, each of which is tailored to a particular medical condition. In one example, expert systems are provided to monitor cardiovascular health and cancer, having separate modules where each module is tailored to management of a different disease. Each module operates using a different set of rules that operate using input from a variety of sensor and knowledge base systems.

FIG. 1 illustrates system 100 having a plurality of data sources 90 coupled to expert system 135. Data sources 90 include but are not limited to, for example, input devices such as implantable sensor 105A, external sensor 105B, physician input 110, patient input 115, patient history 120, pharmaceutical database 125 and population/clinical study data 130.

Sensor 105A and sensor 105B include, in one example, implantable and non-implantable sensors, respectively. Sensor 105A and sensor 105B each provide a signal that is coupled to expert system 135. Sensor 105A and sensor 105B provide signals corresponding to patient vital signs.

Sensor 105A, in one example, includes one or more implantable sensors, such as a transthoracic impedance sensor, a minute ventilation sensor, a respiratory rate sensor, a heart monitor, an accelerometer, an intracardiac pressure sensor and other types of sensors.

Sensor 105B include one or more external, or non-implantable sensors, examples of which include a weighing scale (mass sensor), a blood pressure cuff (or pressure sensor), an external monitor as well as other types of ambulatory sensors. In one example, external sensor 105B includes a weighing scale which may include a digital communication link with expert system 135 or which may provide data that is manually entered into a personal digital assistant (PDA) or otherwise provided to expert system 135.

In various examples, data sources 90 can include a fluid sensor, an accelerometer or a temperature sensor, any of which can be implantable or external. Data sources 90, in various examples, includes sensors to provide data relating to cardiac, cardiopulmonary and cardiorenal health.

Physician input 110 includes an interface or data entry device accessible to a physician, medical personal or other user. Exemplary data entry devices include a keyboard, a mouse, a trackball or other controller, a microphone, a touch-sensitive screen, a removable media storage device, a PDA or other device for providing data to expert system 135. Data entered by the physician includes, for example, prescription information, medical records, patient symptoms, observation data as well as other information. In one example, physician input 110 can be used to specify a particular value or threshold of a parameter for which system 100 generates and provides notification. The physician is able to specify the rules and corresponding levels for generating notifications or alerts for the benefit of the physician, the patient or other user.

Physician input 110, in one example, allows entry of physician-established rules for performance of system 100. For example, the physician may instruct that an alert is generated and sent upon detecting a particular condition, (for instance, blood pressure change in excess of a particular value). Such a rule may allow early detection of a co-morbidity. In one example, physician input 110 can be used to mute an alert for an innocuous condition.

Patient input 115 includes an interface or data entry device accessible to a patient, a proxy for the patient or other user. Exemplary data entry devices include a keyboard, a mouse, a trackball or other controller, a microphone, a touch-sensitive screen, a removable media storage device, PDA or other device for providing data to expert system 135. Using patient input 115, a user is able to enter data corresponding to real time or earlier observations. In one example, patient input 115 includes a PDA executing a program to allow the patient to enter data such as food intake, exercise activity, perceived sensations and symptoms and other noted phenomena. Data from the PDA, or other patient input device, is transferred to expert system 135 by a wired or wireless connection. Patient input 115, as with physician input 110, in various examples, includes a data entry terminal.

Patient history 120 includes an interface configured to receive information including, for example, electronic medical records (EMR), clinical information system (CIS) data, or other data corresponding to a particular patient. Exemplary data includes family medical history, immunization records, patient vital signs, trends and other historical medical and clinical data.

In one example, the hospital or clinic information system includes details concerning the patient's medical history. A bedside computer or other device is sometimes used to collect data in some hospital settings. In one example, lifetime health and medical information for a particular patient is provided electronically.

Pharmaceutical database 125 includes data correlating specific drugs with medical conditions and symptoms. In one example, pharmaceutical database 125 includes data generated based on research corresponding to specific geographical regions of the world, including, for example, the United States. Pharmaceutical database 125 also includes data indicating population pharmaco-kinetics for different drugs. Data included, for example, correlates the effects of a drug as a function of time after having taken the drug. In one example, pharmaceutical database 125 includes data about the drug therapy for a particular patient.

Population/clinical study data 130 includes data indicating relationships between selected drugs, for example. In one example, population/clinical study data 130 includes normative and statistical data showing relationships between populations and particular drugs. In one example, population/clinical study data 130 includes data derived from clinical studies data for a particular population.

Information derived from data sources 90 is provided to expert system 135 by a wired or wireless communication link and includes measured input signals (derived from implantable sensor 105A and external sensor 105B) and information in a knowledge base. The knowledge base includes information from one or more of physician input 110, patient input 115, patient history 120, pharmaceutical database 125 and population/clinical study data 130. Other data sources 90, including for example, physician input 110 and patient input 115 can be construed as either measured input signals or as part of the knowledge base. In one example, patient input 115 includes a sensor (for instance, weight data generated by a scale stepped on by the patient) and it can also be construed as patient history 120 if the scale reading were collected earlier and trended in time. Different combinations of the data sources can function as the knowledge base and as measured inputs. In general, the knowledge base includes a collection of knowledge represented in machine-processable form such as inference rules, facts, or other data representations. The knowledge base is stored in a memory accessible to expert system 135 and, in various examples, includes removable or non-removable memory, random access memory or read only memory.

Expert system 135 includes an inference engine and is implemented, in various examples, in hardware or software. In one example, expert system 135 includes a processor executing an expert system algorithm stored in a memory. Expert system 135 is configured to generate an inference based on the knowledge base and the measured input signals. Exemplary inference engines include a causal probabilistic network such as a Bayesian network, fuzzy logic, a decision tree, a neural network or a self-organized map. In one example, expert system 135 operates on the basis of measured inputs and generates a knowledge base over a period of time.

A Bayesian network includes a conditional probability-based network that relies on Bayes theorem to characterize likelihood of different outcomes based on known prior probabilities (i.e. observed prevalence of a disease) and newly acquired information (i.e. sensor signals). Bayesian networks use causal knowledge and explicitly model probabilistic dependence and independence relationships between different events.

Fuzzy logic provides a mechanism for manipulating uncertain information and variables that do not otherwise permit simple categorization as affirmative or negative. Fuzzy logic describes the application of if-then rules to uncertain information and provides probability of outcomes based on preceding events or conditions. Fuzzy logic relies on probabilistic if-then rules. According to principles of fuzzy logic, the probability that a premise will be true is predictable, and the conclusion that follows will also occur with some probability.

A decision tree provides a method for representing multiple temporal and logical inputs and the possible outcomes based on a combination of those inputs. A decision tree does not entail probabilities associated with branches.

A neural network is a black-box information-processing device having a number of non-linear processing modules connected together by elements that have information storage and programming functions. A self-organized map is a particular type sheet-like neural network array configured to execute an adaptive algorithm capable of learning. The neural network is based on the competitive and unsupervised learning process. Other types of expert systems are also contemplated.

Expert system 135 generates an inference based on a combination of information received from data sources 90. The information derived from data sources 90 is subject to errors and other sources of imprecision. In one example, the information is expressed using probabilities to quantify the uncertainty. For example, data derived from a clinical study might indicate that if a particular level of a parameter is noted, then with a specified level of confidence, the patient is suffering from a particular malady. Data from additional sources will further modify the confidence level of the particular conclusion and further enhance the precision of an identification. In one example, expert system 135 incorporates temporal reasoning for events that have a time lag. For example, information about an event includes a temporal stamp and the time intervals between dependent events is propagated through the network and is marked as a possible cause of a later event.

In FIG. 1, expert system 135 provides an output corresponding to an inference generated on the basis of data sources 90. The output, in one example, includes a recommendation for a change in a regimen administered to the patient. The regimen may specify a therapy or drug protocol and the recommendation may include changes to levels or types of drugs or an adjustment in a protocol for delivery of electrical pulses. In one example, a regimen change includes changing an automated drug delivery regimen. For example, upon detecting a condition known as myocardial infarction, a thrombolitic drug is administered using an implantable pump. In one example, the output includes an alert for delivery to a physician or other medical personnel. The alert provides notification that a change in the regimen is forthcoming or recommended. Notification of a change may include providing an audible, visible or tactile alert using a local or remote device.

In one example, the inference engine initiates a change in the therapy regime. This may include, for example, changing a pacing rate, changing an amplitude, selecting a different set of electrodes, changing a drug, changing a drug dosage or changing another parameter that affects the therapy regimen. One example provides that the frequency of monitoring a physiological or device parameter is changed based on an instruction received from the inference engine. One example provides that the inference engine generates and transmits a message to a monitoring facility. The monitoring facility may include, for example, a physician-accessible computer, cellular telephone, facsimile machine or other communication device coupled to a communication network. The message may include an alert or other signal indicating that a change has been noted or, based on another triggering event, has been detected. For example, a particular combination of drugs in a therapy regimen may have produced an adverse side effect for which the physician is to be notified. In one example, an alert is generated and transmitted to indicate drug resistance upon determining that there is no noticeable effect of a drug taken by a patient.

In one example, expert system 135 provides monitoring of data sources 90. For example, an implantable device may generate and store selected data in a memory for later telemetry to an external storage device or other processor. A processor of a remote interrogation device, programmer or other device can later analyze the data and generate an inference or output based on detected conditions. As a function of the generated data, a flag is set and an alert or other signal is provided to notify a physician.

In one example, upon detecting heart failure or decompensation (based on an impedance, pressure or other signal), an alert is generated and transmitted to a physician. As another example, an alert is generated and transmitted to a physician upon detecting conditions associated with a particular co-morbidity, such as heart failure or renal failure.

As illustrated in FIG. 1, expert system 135 generates output 95 based on the inference derived from data sources 90. Output 95, in one example, includes patient event detection 140, physician alert 145, drug side effects 150 and tailored medical regimen 155. System 100 provides patient event detection 140, which includes both events and conditions, based, in part, on learned patterns and sensor data. Exemplary event detections included decompensation, chronic obstructive pulmonary disease, pneumonia and other events or conditions. Following detection of an event, system 100 generates physician alert 145. Alert 145, in various examples, includes a wired or wireless signal that is communicated to a physician or other medical personnel. The alert may include a visual, audible or tactile signal such as a message displayed on a monitor, a light appearing on a panel, a characteristic tone or sound presented on a cellular telephone or other device or a vibration to draw the attention of the physician or other medical personnel. At 150, the output includes an indication of drug side effects associated with a particular therapy regimen. The side effects may be associated with a current regimen, a proposed regimen or a regimen determined to be a likely treatment protocol. At 155, the output includes a medical regimen selected as a function of the physician's input and expert system 135. In one example, an inference generated by expert system 135 is supplied to an output device, such as physician alert 145, which communicates with a remote portable device carried by a physician. The output device, in one example, includes a wireless transmitter or server coupled to a communication network. In addition, the communication network is accessible to the physician or other medical personnel. For example, the communication network can include a local network (such as a local area network or LAN) or a wide area network (such as the Internet) accessible from a medical facility. In one example, the output device includes a programmer configured for changing programming of a pulse generator for the patient or issuing an instruction to an implantable device.

Figure 2:
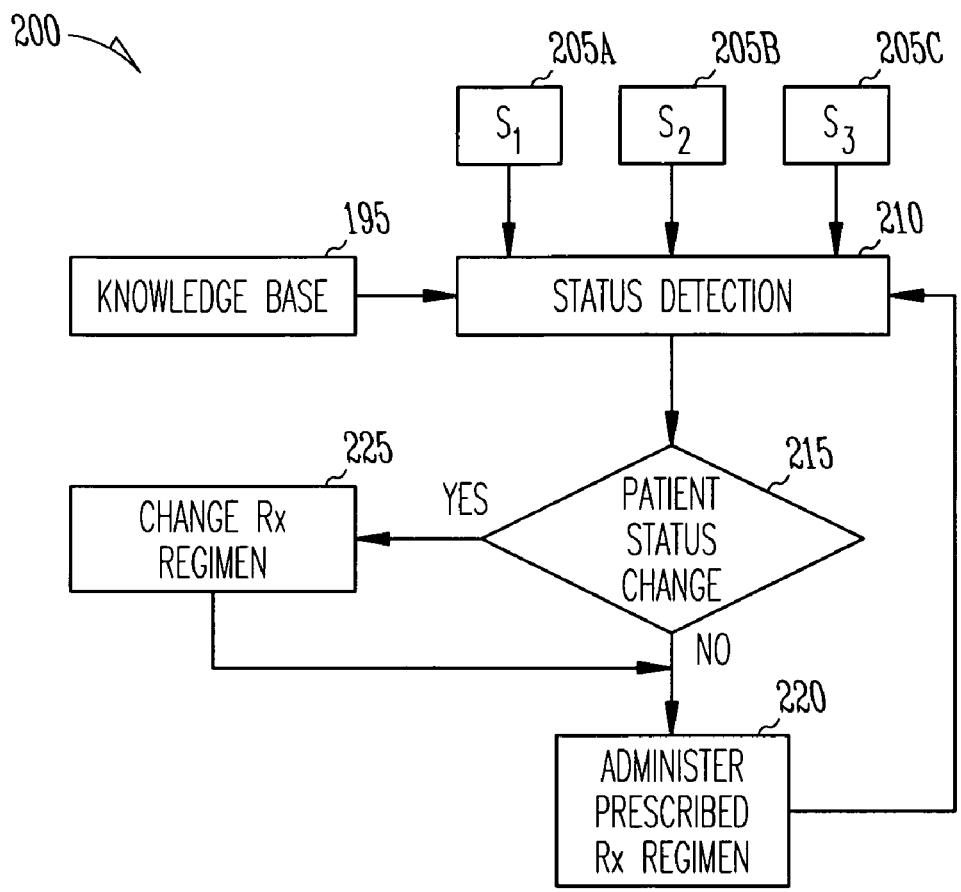
FIG. 2 illustrates a flow chart of a method according to one example of the present subject matter.

FIG. 2 illustrates method 200 utilizing an expert system. Sensor S1 205A, sensor S2 205B and sensor S3 205C each provide a signal to status detection block 210. Sensors 205A, 205B and 205C, for example, each include a particular heart sensor or other monitoring device. In particular, sensor S3 205C is associated with detecting heart sounds. Status detection block 210, in one example, represents an output provided by expert system 135 based on input signals received from sensor S1 205A, sensor S2 205B and sensor S3 205C as well as knowledge base 195. Knowledge base 195 includes patient history, medical data as well as other data, some examples of which are noted elsewhere in this document.

After having received the input signals from the sensors and developed an inference as to the patient's state, processing continues at 215 where a query is presented to determine if the patient status has changed since a previous status check. If the outcome of the query is affirmative, then, in one example as shown at 225, the therapy regimen is changed to compensate or otherwise improve the patient's health. If, on the other hand, the outcome of the query is negative, or following any adjustment at 225, the method continues at 220 where the prescribed therapy regimen is administered to the patient. Following 220, method 200 returns to 210 where the patient status is again detected or checked.

Figure 3A:
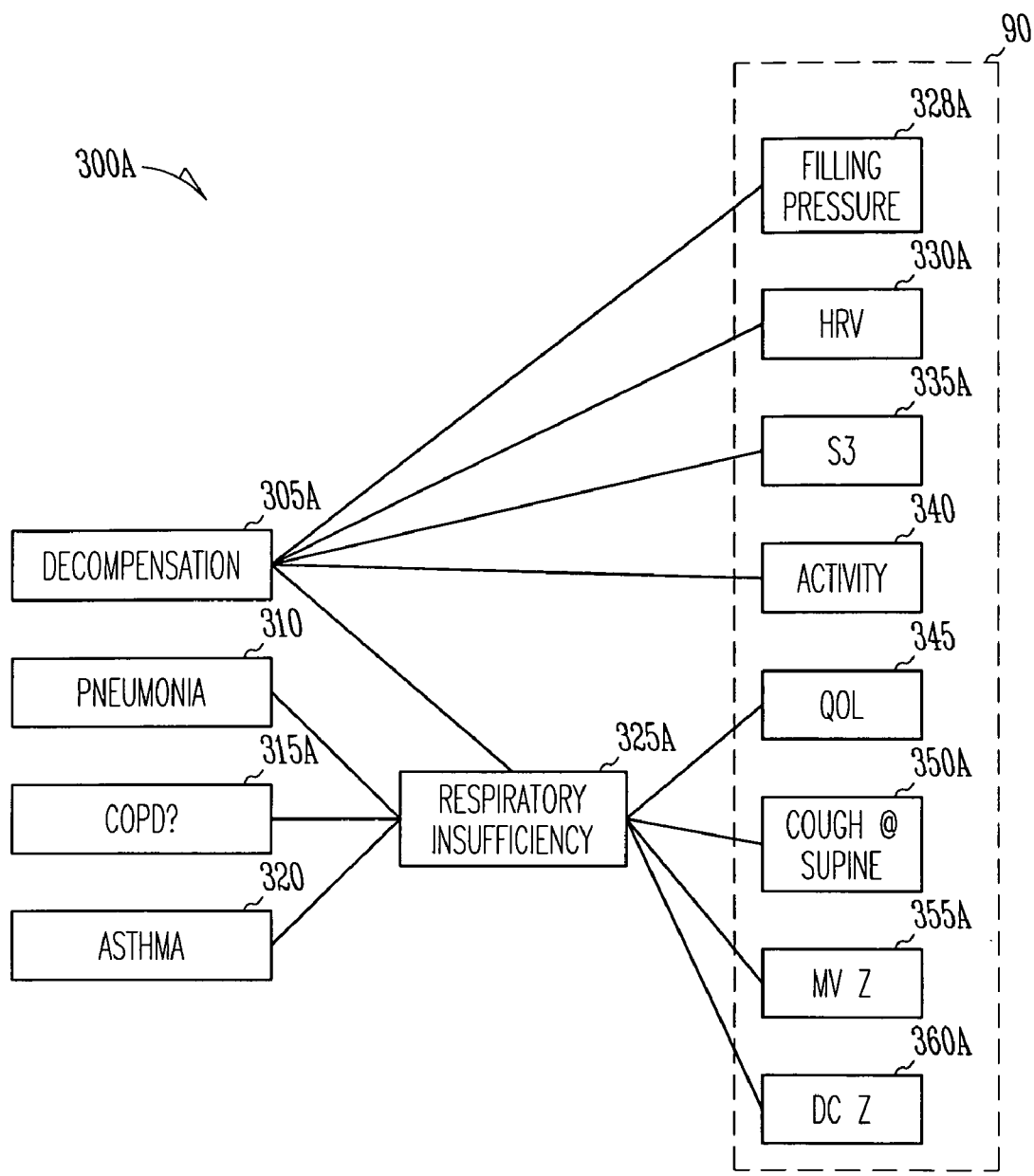
FIGS. 3A and 3B illustrate block diagrams associated with exemplary systems based on a Bayesian network.
Figure 3B:
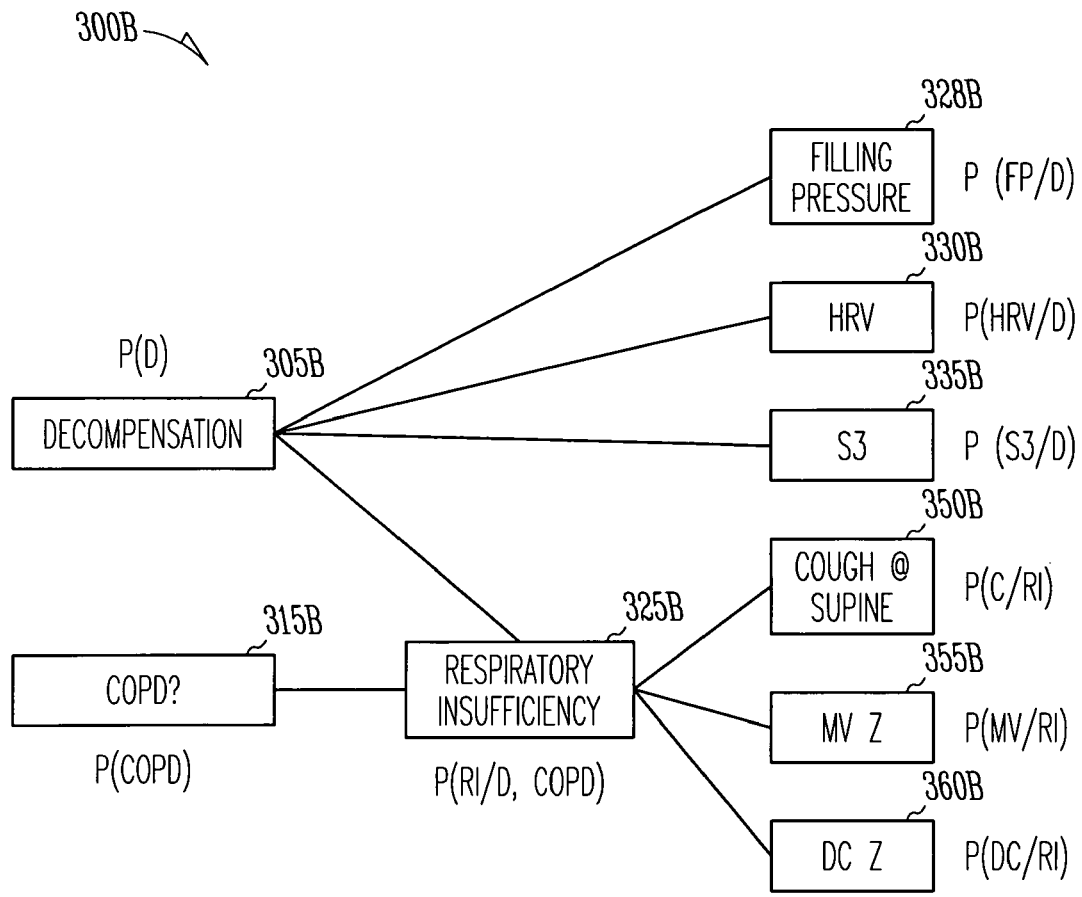

FIGS. 3A and 3B illustrate an expert system that analyzes relationships between exemplary physiological phenomena or conditions and selected parameters.

FIG. 3A illustrates diagram 300A in which an expert system includes a Bayesian network and data sources 90 includes filling pressure sensor 328A, sensor HRV 330A configured to monitor heart rate variability, heart sounds S3 335A, activity level 340, quality of life 345, cough at supine 350A, minute ventilation (transthoracic impedance) 355A and DC impedance 360A. For sake of clarity, a knowledge base accessible to expert system 135 is not illustrated in the figure. With a specific probability, the system in FIG. 3A can detect patient decompensation 305A based on the data derived from, in part, the combination of sensors in data sources 90. Expert system 135 implements a set of rules corresponding to the different data sources to make this determination. Unlike neural networks, a Bayesian network explicitly models causality between events (nodes). In a Bayesian network, events that are assumed to be independent are not connected, thus reducing computational complexity, in one example, from 255 dependent parameters to 18 parameters to be specified.

In FIG. 3A, for example, the physiological phenomena includes decompensation 305A, pneumonia 310, chronic obstructive pulmonary disease (COPD) 315A and asthma 320. As indicated by the arrows, each of pneumonia 310, chronic obstructive pulmonary disease 315A and asthma 320 can, either individually or in combination, result in respiratory insufficiency 325A. In addition, respiratory insufficiency 325A can be detected using sensors that monitor for cough at supine 350A, minute ventilation (transthoracic impedance) 355A, DC impedance 360A and quality of life 345. In one embodiment, the sensors that monitor for cough at supine 350A, minute ventilation (transthoracic impedance) 355A and DC impedance 360A are each disposed in an implantable device.

As indicated by the arrows, sensors responsive to filling pressure sensor 328A, heart rate variability 330A, heart sounds S3 335A and activity level 340 are used in determining the presence of decompensation 305A.

FIG. 3B illustrates diagram 300B demonstrating probabilistic reasoning in disease diagnostics. In FIG. 3B, nomenclature representing probability is indicated for the various conditions. For example, the initial probability that the patient is experiencing decompensation 305B is denoted as P(D) and the probability that the patient is experiencing chronic obstructive pulmonary disease 315B is denoted as P(COPD). These prior probabilities are obtained, for example, from statistics on disease prevalence in a population. Furthermore, the conditional probability of exhibiting respiratory insufficiency during decompensation or COPD 325B is denoted as P(RI/D, COPD). In various examples, this information is obtained from clinical studies, expert opinions, or other databases. The combination of external and implantable sensor signals is used to enhance the accuracy of diagnosis. The information regarding the conditional probability of sensor detection during decompensation is derived, in various examples, from clinical studies, expert opinions or literature. Thus, the probability of reduced heart rate variability 330B during decompensation 305B is denoted as P(HRV/D). The probability of detection of S3 heart sound 335B during decompensation 305B is denoted as P(S3/D). The probability of increased filling pressure 328B during decompensation 305B is denoted as P(FP/D). The probability of cough at supine 350B during exhibiting respiratory insufficiency 325B is denoted as P(C/RI). The probability of changes in minute ventilation signal (transthoracic impedance) 355B indicative of breathing difficulty during respiratory insufficiency 325B is denoted as P(MV/RI). The probability of lowered DC impedance 360B during respiratory insufficiency 325B is denoted as P(DC/RD). Numerical values can be generated for each probability.

Diagram 300B also demonstrates enhanced specificity and sensitivity of diagnosis based on information acquired from various sensors. With reference to FIG. 3B, Table 1 illustrates affirmative and negative outcomes for selected probabilities. In the example shown in Table 1, and for a particular population, the prevalence of decompensation is 30% and the prevalence of non-decompensation is 70%.

TABLE 1

|  | Yes | No |
|---|---|---|
| P(D) | 0.3 | 0.7 |

In addition, and for one example, the probability of decreased heart rate variability during decompensation is quantified in Table 2.

TABLE 2

| P(HRV/D) | D = Yes | D = No |
|---|---|---|
| HRV = Yes | 0.6 | 0.3 |
| HRV = No | 0.4 | 0.7 |

The joint probability P(HRV,D) is computed as P(HRV/D)*P(D), as shown in Table 3.

TABLE 3

| P(HRV, D) | D = Yes | D = No |
|---|---|---|
| HRV = Yes | 0.6 * 0.3 | 0.3 * 0.7 |
| HRV = No | 0.4 * 0.3 | 0.7 * 0.7 |

In one example, and for an individual patient, the population statistics are updated when a particular sensor signal is flagged (i.e. decreased heart rate variability).

Based on the tabulated data, the following Bayesian rules are used in the probability update for this example:

1. Compute joint probability P(HRV,D)=P(HRV/D)*P(D) as shown in Table 3.
2. Compute probability of HRV. For the data shown, P(HRV)=(0.6*0.3+0.3*0.7, 0.4*0.3+0.7*0.7)=(0.39, 0.61).
3. Compute individual probability of decompensation, P(D/HRV=y)=P(HRV=yes,D)/P(HRV=y)=(0.46, 0.54).

As a result, the calculated probability of decompensation is increased from 0.3 to 0.46 based on the sensor data.

Other sensor signals associated with decompensation can also be detected to further enhance the specificity and sensitivity of decompensation detection. Exemplary additional information for use in the computation includes time lag between the events, individual pharmacogenomics and other data. Pharmacogenomics refers to a body's response to a drug based on the interaction of pharmaceuticals and genetics for that particular individual.

Figure 4:
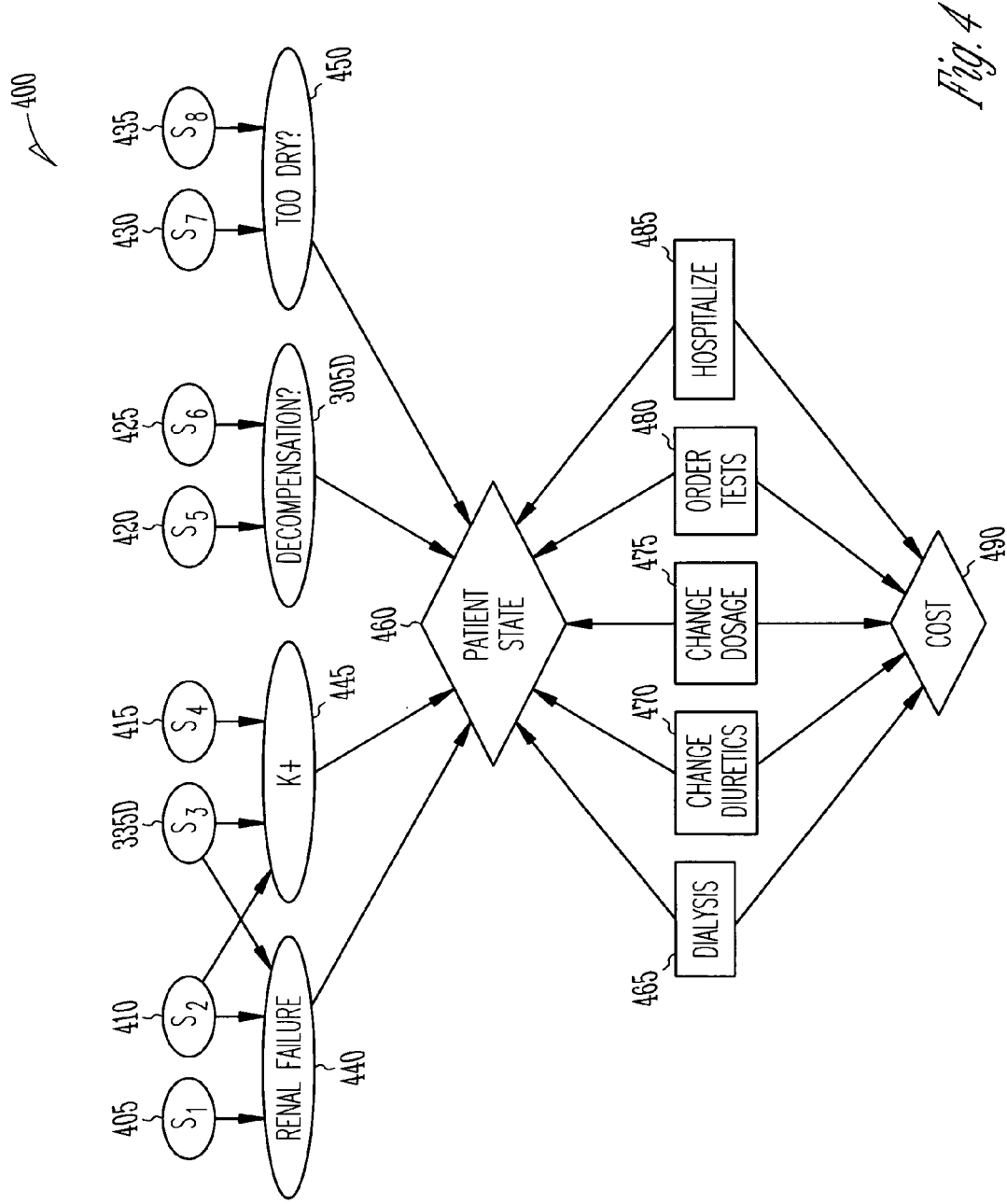
FIG. 4 illustrates an example of decision-making in patient management, including drug management.

FIG. 4 illustrates diagram 400 demonstrating decision-making processing for patient management. As indicated in FIG. 4, renal failure 440 is detected using sensor S1 405 and sensor S2 410. In addition, a potassium level 445 is detected using sensor S3 335D and sensor S4 415. Decompensation 305D is detected using sensor S5 420 and sensor S6 425.

Fluid level 450 is detected using sensor S7 430 and sensor S8 435. The patient state at 460 is based on a combination of physiological phenomena as measured by sensors S1 405, S2 410, S3 335D, S4 415, S5 420, S6 425, S7 430 and S8 435. In the example illustrated, treatment options considered for this particular patient include dialysis 465, changing diuretics 470, changing dosage 475, ordering a particular test 480 and hospitalization 485. In each case, cost 490 is considered in evaluating a treatment option. In this example, the goal is to choose a cost-effective treatment regimen based on the diagnosis derived from sensor signals without compromising quality of care.

Each sensor can provide information relevant to analysis of one or more physiological conditions. For example, and as illustrated, sensor S2 410 provides information relative to potassium level 445 as well as renal failure 440. In the example illustrated, eight sensors are shown, however, in a particular implementation, there may be hundreds of sensors, any number of which are cross-linked to multiple physiological conditions.

The information from the sensors is combined to derive a regimen for treatment or further monitoring. For example, a pacing mode can be determined using data sources 90 and expert system 135. In the example of FIG. 4, multiple treatment regimen options are presented, any one of which is selected based on monetary cost. For example, hospitalization 485 may be the most expensive, and thus, one of the remaining three options is selected based on other criteria. For example, and for some patients, a particular drug or therapy regimen is prescribed rather than recommending treatment by dialysis. Other criteria or attributes can also be applied to facilitate selection of a regimen. For example, criteria can be applied to optimize patient safety or achieve a targeted morbidity or mortality rate.

Figure 5:
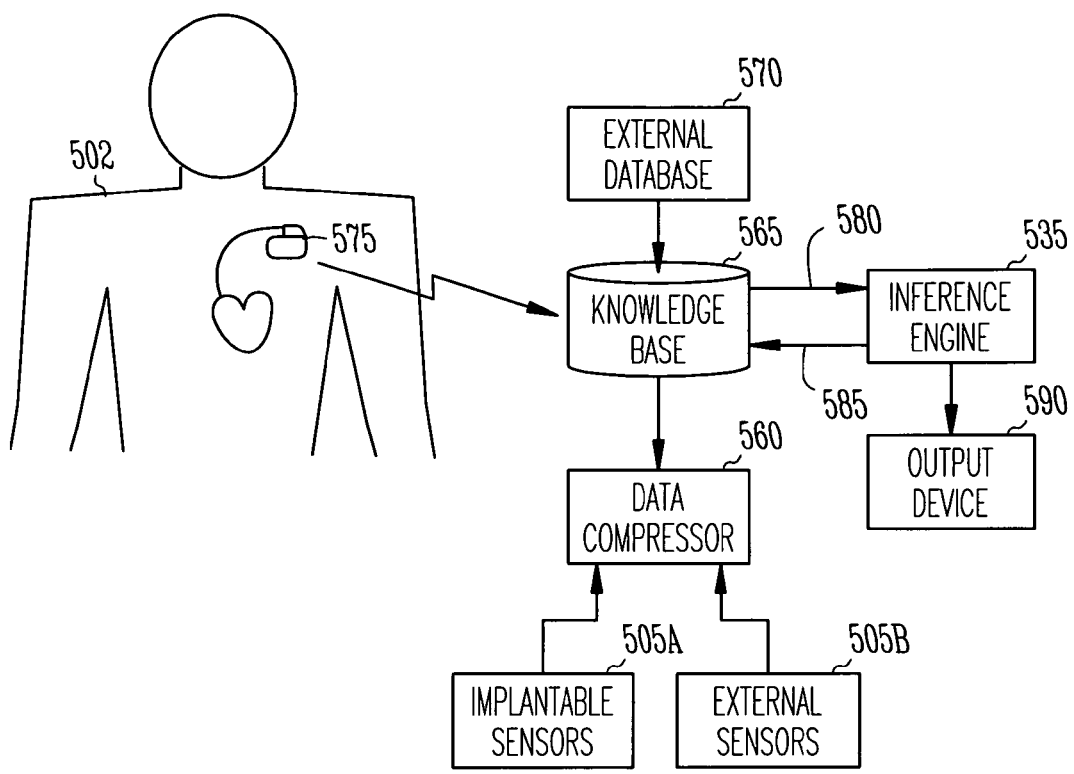
FIG. 5 illustrates a diagram of an exemplary system.

FIG. 5 illustrates an exemplary system configured for use with patient 502. Implantable device 575 provides therapy or monitoring for patient 502. Device 575 is in communication with knowledge base 565. In one example, implantable device 575 includes a memory configured for storage of the contents of knowledge base 565 and in one example, knowledge base 565 includes data stored in a remote server or other storage device. Knowledge base 565 receives data from external database 570. In various examples, external database 570 includes patient history, a pharmaceutical database or population/clinical study data.

Knowledge base 565, in one example, receives data from external sensors 505B or implantable sensors 505A. In one example, external sensors 505B and implantable sensors 505A are coupled to knowledge base 565 by data compressor 560. Data compressor 560, in one example, provides real time data compression using characteristic points, as described in U.S. patent application Ser. No. 10/607,820, entitled "SIGNAL COMPRESSION BASED ON CURVATURE PARAMETERS," by Sweeney, filed Jun. 27, 2003, and U.S. patent application Ser. No. 10/607,818, entitled "USE OF CURVATURE-BASED SIGNIFICANT POINTS FOR TACHYARRHYTHMIA DETECTION AND DISCRIMINATION," by Sweeney et. al., filed Jun. 27, 2003, each of which are incorporated herein by reference. Other forms of data compression are also contemplated. Data compressor 560, in various examples, compresses external sensor data, implantable sensor data or knowledge base data. In one example, the compressed data is stored internally in a memory of the implantable device.

Inference engine 535 is coupled to knowledge base 565 and executes an expert system algorithm. Inference engine 535 receives data from knowledge base 565 via link 580 and is coupled to output device 590. Output device 590, in various examples, includes a communication network connection or transducer for notifying or signaling a physician, patient 502 or other personnel. Inference engine 535, in one example, also provides a feedback signal via link 585 to knowledge base 565. Data fed back to knowledge base 565, from inference engine 535, is based on an inference generated by inference engine 535 and, in various examples, includes trend data, correlation data and other data that augments, replaces or adjusts the data in knowledge base 565. In one example, the feedback signal includes a weighting factor that corresponds to a scaling parameter or a probability and the weight ascribed to an input signal (from an input device) is adjusted based on the feedback signal.

Exemplary Alternatives

The knowledge base, external sensors, and inference engine can be contained in the same or different housing. In one example, the inference engine and knowledge base or distributed in different locations and communicate by an analog or digital network.

In one example, any combination of external and implantable sensors are used. In addition, data derived from one data source can be used to modify data derived from another sensor. For example, data can be received by evoking responses to a set of questions presented to the patient or other user (including a physician). If a patient provides data in a manner to indicate that their general heath perception is at level 3 on a scale of 1 to 5, then expert system 135 responds by presenting an additional set of questions for evaluating the patients health. The additional set of questions may be presented to the patient immediately or at a later time. By way of another example, if one sensor indicates a particular condition may be present, or a threshold value is exceeded, then the frequency of data sampling of a particular sensor is adjusted. By dynamically adjusting the data provided by data sources 90, expert system 135 can tailor the analysis of the data and reporting of detected conditions.

In one example, the system provides a monitoring function or facilitates decision-making by a physician. For example, a program performs an optimization routine and determines, for instance, minimum conditions for alerting a physician of a detected condition. In one example, expert system 135 is configured to monitor for the effects associated with intake of a particular drug and, based on data derived from a database, expert system 135 is configured to monitor for side effects, for example, within approximately 2 hours after a patient receives a beta-blocker.

In one example, expert system 135 provides data to optimize patient management based on the data provided by data sources 90. For example, if expert system 135 determines that the patient has had renal failure, then an output provided by expert system 135 and generated on the basis of information provided by data sources 90, may provide guidance for selecting between prescribing diuretics or providing dialysis.

The inference generated by expert system 135, in one example, evolves over time with the accumulation of additional data in the knowledge base. For example, rules and knowledge implemented by expert system 135 may be modified over time and thus, it can be described as capable of learning. A Bayesian network, for example, is capable of learning as the relationship between selected nodes evolves.

In one example, inferences generated by expert system 135 evolve over time based on performance history with a particular patient. For example, predetermined weighting factors are used with certain input signals (which may differ from another patient) and after a period of time, (days, weeks and months in various examples) during which the system is learning, the parameters stabilize and the confidence level for an inference is improved.

In one example, expert system 135 yields an improved calculation of posterior probability based on experience. Pursuant to Bayesian probability theory, the posterior probability is the probability of some event occurring after empirical data, derived from data sources 90 and prior probabilities have been considered.

Expert system 135 receives rules to implement the expert system. The rules may be received in the form of operating parameters or the system may acquire rules over a period of time.

In one example, expert system 135 is configured to learn based on history with existing sensors and also learn with the addition of data from new sensors, such as, for example a vibration sensor. In one example, the addition of a new sensor causes expert system 135 (including an adaptive tree structure) to refine the importance associated with the various inputs and adaptively change the way the inputs relate to each other in the network. In one example, expert system 135 is configured to identify a trend based on sensor data. In one example, expert system 135 identifies a trend from individual sensor data and provides feedback that is used to update the knowledge base for a particular population. For example, if a correlation is noted as between spirometer data and a minute ventilation signal for a particular patient (or a group of patients), then data corresponding to that correlation is propagated to other patients or groups of patients. The propagated data is stored in the knowledge base. In one example, the knowledge base is developed for a population or grown by receiving feedback based on sensor data and analysis from particular patients. In one example, the knowledge base is developed and grown by receiving feedback from specific sensor devices based on a specific population.

Consider an example including a bathroom scale and a blood pressure cuff as data sources 90. The data from the scale and the cuff are each weighted (with a probability or other factor) and combined in a particular manner. In this example, the blood pressure data is given more weight (0.8% probability) in detecting deterioration of a particular condition and the bathroom scale is given less significance (0.2% probability) in part, because the patient is known to have renal insufficiency. The weighting is applied by expert system 135 based on programming and learning. The data is weighted to specifically change those signals to characterize the patient's current state.

Expert system 135 receives the raw data from the bathroom scale and the blood pressure cuff and attributes the appropriate weight (here, probability) to each input. Expert system 135 establishes a hierarchy which, in this example, is based on time or prior history factors. For example, myocardial infarction could result in acute decompensation and thus its weight is elevated for some period of time after having occurred. On the other hand, myocardial infarction could result in remodeling and dilated cardiomyopathy leading to decompensation. Retention of event temporal information allows for updates in decision-tree hierarchy.

The frequency of patient visits to a hospital, clinic or other medical facility, along with their current medication regimen, can serve as an input signal. For example, the frequency of follow-up visits is indicative of the treatment regimen. In particular, if the patient is healthy, then no change in frequency will be noted, but if the patient is not healthy, then part of the treatment regimen may entail more frequent visits. Thus, one example provides that the treatment regimen includes instructing the patient to increase the frequency of visits.

In various examples, expert system 135 is included in an implantable device, a remote interrogation device, a computer or a server located at a clinic or other facility. Portions of expert system 135 can be distributed in more than one device (implantable or external) and located at multiple locations.

Expert system 135 receives sensor data that may be processed or unprocessed. In one example, the data from a sensor includes actual measured data without regard for any threshold values. In one example, data from a sensor includes an indication that the value is greater or less than a particular threshold value.

The output generated by expert system 135 indicates detection of an event based on a combination of input signals. For example, expert system 135 may detect deterioration in a chronic state based on a combination of multiple signals.

In one example, expert system 135 is configured to recognize a pattern of health data for a patient. For example, if endocarditis is detected, then the patient is likely to develop acute mitral deterioration followed by left atrial dilation which further leads to long term heart failure. This development path is embodied in the expert system and appropriate alerts are programmed to be delivered upon detected conditions.

If, for example, it is known that heart failure is associated with lowered heart rate variability, then sensors corresponding to audible heart sounds, cough at supine and impedance may all indicate a change. An expert system can determine the probability that a particular patient has decompensated based on the sensor data.

The expert system applies backward propagation to determine outcomes for a specific patient. Based on measured data and observed events, the expert system enhances its knowledge as to particular conditions.

Expert system 135, in one example, is configured to learn with experience and data accumulation. For example, based on a product of a probability associated with a patient (and derived from a population study) and a measured parameter, the knowledge associated with that condition is improved.

Expert system 135 is configured to discern inconsistent data received from the sensors and provide an alert when appropriate. In one example, probabilities are assigned to sensors based on the maturity of the experienced with that situation. In one example, more than one expert system 135 is implemented and sensor data is combined and an arbitration module selects an output based on the inferences generated by the multiple expert systems.

In one example, after a sufficiently long learning period, expert system 135 is capable of generating an output without regard for the probabilities associated with different input signals. In one example involving a Bayesian network, some of the links established early in the learning process are attenuated and eventually drop out altogether and the system effectively simplifies itself.

In one example, expert system 135 evolves over time and exhibits adaptive learning. For example, where an expert system initially functions as a Bayesian network, over time it migrates to a decision tree network or other form of expert system. As another example, the system may begin operating using simplistic rules until the database is sufficiently mature, after which the database migrates to a probability network on the basis of a priori knowledge. Physician input 110, as well as other data sources 90 can inform the system as to performance.

In one example, physician input 110 can affect an alert (for example), or some other functionality of the expert system. Physician input 110 can be used to construct if-then rules such as those instructing when the physician is to be notified for a particular condition.

The combination of sensor data is analyzed to determine the patient state. For example, if a change is noted in two parameters, then, based on the nature of those changes, and the relative timing of those changes, expert system 135 reconciles the patient state and generates a prediction for future events or conditions.

For example, a change in blood pressure may be followed by coughing. Expert system 135 provides analysis to identify the causal linkage between these inputs. The causal linkage facilitates future predictions.

In one example, an implantable device includes an intercardiac pressure sensor, a heart sound sensor, a heart rate variability sensor and a DC impedance sensor and the external sensors include a bathroom scale, a blood pressure cuff and a blood analysis sensor. The data received from the implantable device is collected at a remote interrogation device and communicated to a server or other processor. Date from the external sensors is combined with the implantable device data at the server. The server processes the data, accesses a knowledge base including patient history and population data, and generates an inference based on an expert system algorithm. The server also provides an alert to the physician upon detection of a particular condition.

Expert system 135 also generates an output based on drug side effects. For example, if a patient became ill two hours after taking a particular drug, then expert system 135 associates the illness with the drug and identifies it as a side effect with some probability. In addition, expert system 135 notifies the physician that the drug exhibits a side effect with some probability. Furthermore, the mere fact that there was a side-effect is an outcome that can be characterized by a time and severity. In one example, expert system 135 learns that the drug is associated with a side effect and an appropriate rule may be implemented by way of physician input 110. The fact that the patient took the drug, any observable side effect, and the time of observation or occurrence of any side effect, can all be noted by the patient as an input using patient input 115.

In addition to drug side effects, other conditions or events also generate alerts for the physician. Examples of alerts include detection of a malignant event and other co-morbidities.

In one example, an alert signal is sent to a physician or other medical personnel via an output device in communication with expert system 135. Exemplary output devices include a cellular telephone, a facsimile machine, a telephone, a pager and a pager and the alert message can be conveyed in the form of an automated telephone call, a voice mail message, a pager signal, a facsimile document, an e-mail or an instant message.

In various examples, the treatment regimen may include issuing an instruction to the patient to either take a particular medication or not take the medication.

In one example, expert system 135 provides an output using a touch-sensitive display device that is accessible to a user, such as a patient or a physician. A processor driving the display device generates prompts for user entry of reply data which is then used to generate an inference.

In one example, data corresponding to selected events or conditions is provided to the physician or to the patient. Notification provided to the physician or patient is derived from filtered or extracted sensor data. According to one example, notification entails providing a summary of selected data to the physician. The summary is generated by the implantable device or by an external device such as a server. The physician can respond to the notification by requesting additional data from the knowledge base or by requesting additional sensor data. In one example, notification provides summary data without inundating the physician with excessive data requiring evaluation and analysis. Thus, the expert system performs the extraction and analysis of the data and reduces the time required for the physician to assess the condition or event.

In one example, the inference engine provides adaptive feedback to the knowledge base. For example, following detection of a particular condition, the expert system provides feedback to the knowledge base which is then used in later analysis. In one example, the feedback is provided to the particular system for a single patient. In one example, the feedback is propagated, or otherwise provided to other systems for the benefit of more than one patient. Thus, changes in the knowledge base can be derived from the experiences of other patients.

Previously unidentified correlations and trends may be identified using the present system. In one example, the inference engine provides data used to select a configuration of external and implantable sensors. For example, sensor weighting is adjusted by a feedback signal from the inference engine, based on detected events, conditions or timing. In one example, edema can be detected based on a change (such as a reduction) in impedance preceded by a change in heart sounds. Thus, detection of a change in heart sounds can be used to amplify, or increase, the weight accorded to data provided by an impedance sensor. Other changes or trends may also be identified by the inference engine with experience. In one example, correlations between different sensors and knowledge based data can be identified. For example, spirometer data can be correlated to minute ventilation (MV) sensor data. With additional experience using a particular set of sensors, other trends and correlations can also be identified.

It is to be understood that the above description is intended to be illustrative, and not restrictive. For example, the above-described examples, or any portion thereof, may be used in combination with each other. In the appended claims, the phrase "any combination" includes a single element as well as multiple elements. Furthermore, the transitional term comprising is used in the open ended sense in that elements in addition to those enumerated may also be present. Other examples will be apparent to those of skill in the art upon reviewing this document.

What is claimed is:

1. A system comprising:
   a plurality of input devices each of which provides an input signal based on a patient state, the plurality of input devices including at least one implantable sensor and at least one external sensor;
   a knowledge base corresponding to the plurality of input devices;
   an inference engine coupled to the plurality of input devices and having access to the knowledge base, wherein the inference engine includes a processor implement a conditional probability algorithm to generate an inference of a patient condition based on application of the algorithm to the knowledge base and at least one input signal provided by said input devices, wherein the knowledge base is adjusted for use in later analysis by using an adaptive feedback signal derived from the inference, and wherein the adaptive feedback signal includes a weighting factor to adjust a weight ascribed to the input signal by the knowledge base; and an output device to generate an output to indicate a therapy based on the inference and to provide the output to a user or a process to provide the therapy.

2. The system of claim 1, wherein at least one input device includes a heart failure sensor.

3. The system of claim 1, further including a storage device having at least one inference rule stored thereon, the inference rule configured to generate the inference.

4. The system of claim 1, wherein the input signal includes temporal information.

5. The system of claim 1, wherein at least one input device is configured to receive data from a user.

6. The system of claim 1, wherein at least one input device is coupled to the inference engine by a wireless telemetry link.

7. The system of claim 1, wherein at least one input device includes a blood pressure sensor, a mass sensor, a fluid sensor, an accelerometer, a temperature sensor, an impedance measuring device or a data entry terminal configured for operation by the patient.

8. The system of claim 1, wherein the knowledge base includes an expression of a probability corresponding to an input signal or an expression of a relationship between at least two input signals.

9. The system of claim 1, wherein the knowledge base includes at least one of patient history, pharmaceutical data, population data, pharmacogenomics data, cost data and clinical study data.

10. The system of claim 1, wherein the knowledge base includes treatment options, and wherein the processor is configured to determine the recommended therapy from the knowledge base and the inference of the patient condition.

11. The system of claim 1, wherein the inference engine is configured to generate an inference in real time.

12. The system of claim 1, wherein the inference engine includes programming to identify a trend or to assign a probability to an input signal.

13. The system of claim 1 further including a communication network coupled to at least one of the output device or at least one input device.

14. The system of claim 13, wherein the communication network is coupled to a medical facility.

15. The system of claim 1, wherein the output device is configured to present a prompt and wherein an input device is configured to receive a user-entered reply.

16. The system of claim 1, wherein the output device is configured to generate an alert based on the inference.

17. The system of claim 16, wherein the therapy regimen includes delivering an electrical pulse or delivering a drug.

18. The system of claim 1, wherein the knowledge base is adjusted using adaptive feedback data derived from the inference, and wherein the adaptive feedback data includes at least one of trend data and correlation data.

19. The system of claim 1, further including a data compressor coupled to the knowledge base.

20. A method comprising:
receiving a plurality of input signals from a patient, at least one input signal generated by an implantable sensor and at least one input signal generated by an external device;
executing a program to generate an inference of a patient condition, wherein the program runs on a processor to implement a conditional probability algorithm and to generate the inference based on an application of the algorithm to the plurality of input signals and a knowledge base;
adjusting the knowledge base for use in later analysis by using an adaptive feedback signal, the adaptive feedback signal generated based on the inference of the patient condition and including a weighting factor to adjust a weight ascribed to at least one of the input signals by the knowledge base; and
producing an output to indicate a therapy based on the inference, and providing the output indicating the therapy to a user or process to provide the indicated therapy.

21. The method of claim 20, wherein receiving the plurality of input signals includes receiving user entered data.

22. The method of claim 20, wherein receiving the plurality of input signals includes receiving cardiac, cardiopulmonary and cardiorenal data.

23. The method of claim 20, wherein receiving the plurality of input signals includes receiving a wireless signal.

24. The method of claim 20, further including providing a prompt to enter data.

25. The method of claim 20, wherein combining the plurality of signals includes accessing a knowledge database corresponding to the patient.

26. The method of claim 20, wherein producing the output includes notifying a physician.

27. The method of claim 20, wherein producing the output includes providing an instruction to an implantable device.

28. The method of claim 20, further including adjusting the knowledge base using adaptive feedback data derived from the inference, and wherein the adaptive feedback data includes at least one of trend data and correlation data.

29. The method of claim 20, further including compressing data stored in the knowledge base.

30. A device comprising:
means for receiving a plurality of input signals from a patient, at least one signal corresponding to an implantable sensor and at least one signal corresponding to an external sensor;
means for storing a knowledge base having data corresponding to at least one input signal;
means for generating an inference of a patient condition using a conditional probability algorithm, wherein the inference is based on application of the algorithm to the plurality of input signals and the knowledge base;
means for adjusting the knowledge base for use in later analysis by using an adaptive feedback signal, the adaptive feedback signal generated based on the inference and including a weighting factor to adjust a weight ascribed to at least one of the input signals by the knowledge base; and
means for communicating an output to a remote device, the output indicating a therapy to a user and wherein the indicated therapy is based on the inference.

31. The device of claim 30, further including a wireless telemetry system coupling at least one signal of the plurality of signals to the means for generating the inference.

32. The device of claim 30, wherein the means for communicating the output includes a wireless transceiver.

33. The device of claim 30, wherein the means for communicating the output includes a telemetry system in communication with an implantable device.

* * * * *

UNITED STATES PATENT AND TRADEMARK OFFICE
CERTIFICATE OF CORRECTION

PATENT NO. : 7,433,853 B2  Page 1 of 1
APPLICATION NO. : 10/889353
DATED : October 7, 2008
INVENTOR(S) : Brockway et al.

It is certified that error appears in the above-identified patent and that said Letters Patent is hereby corrected as shown below:

On the Title page, in "Assistant Examiner", in column 2, line 1, delete "Fernanadez" and insert -- Fernandez --, therefor.

In column 14, line 60, in Claim 1, after "processor" insert -- to --.

Signed and Sealed this

Thirteenth Day of January, 2009

JON W. DUDAS
*Director of the United States Patent and Trademark Office*